(12) United States Patent
Nyholt (10) Patent No.: US 8,995,225 B2
(45) Date of Patent: Mar. 31, 2015

(54) PIVOTING ULTRASONIC PROBE MOUNT AND METHODS FOR USE

(75) Inventor: John James Nyholt, Seabrook, TX (US)

(73) Assignee: BP Corporation North America Inc., Houston, TX (US)

( * ) Notice: Subject to any disclaimer, the term of this patent is extended or adjusted under 35 U.S.C. 154(b) by 454 days.

(21) Appl. No.: 13/463,002

(22) Filed: May 3, 2012

(65) Prior Publication Data

US 2012/0287756 A1 Nov. 15, 2012

Related U.S. Application Data

(60) Provisional application No. 61/484,504, filed on May 10, 2011.

(51) Int. Cl.
| | |
|---|---|
| *G01N 29/265* | (2006.01) |
| *G01N 29/07* | (2006.01) |
| *G01N 29/22* | (2006.01) |
| *G10K 11/00* | (2006.01) |

(52) U.S. Cl.
CPC .............. *G01N 29/265* (2013.01); *G01N 29/07* (2013.01); *G01N 29/221* (2013.01); *G01N 2291/044* (2013.01); *G01N 2291/101* (2013.01); *G10K 11/004* (2013.01)
USPC ......................................... 367/104; 367/120

(58) Field of Classification Search
USPC .............................. 367/87, 104, 120; 403/122
See application file for complete search history.

(56) References Cited

U.S. PATENT DOCUMENTS

| | | | |
|---|---|---|---|
| 3,068,370 A | | 12/1962 | McInnish |
| 3,938,372 A | * | 2/1976 | Sproule .......................... 73/633 |
| 4,292,679 A | * | 9/1981 | Kondo et al. ................. 367/188 |
| 4,852,416 A | | 8/1989 | Boone et al. |
| 5,121,634 A | | 6/1992 | Sasaki et al. |
| 5,515,340 A | * | 5/1996 | Kim et al. ..................... 367/104 |
| 6,227,501 B1 | * | 5/2001 | Malcolm ...................... 248/27.3 |
| 6,626,834 B2 | * | 9/2003 | Dunne et al. .................. 600/444 |
| 2002/0143252 A1 | * | 10/2002 | Dunne et al. .................. 600/437 |
| 2005/0124889 A1 | * | 6/2005 | Flesch ........................... 600/445 |
| 2008/0196504 A1 | * | 8/2008 | Johnson et al. ................. 73/588 |
| 2008/0307637 A1 | | 12/2008 | Fogarty et al. |

FOREIGN PATENT DOCUMENTS

| | | |
|---|---|---|
| EP | 0936529 A1 | 8/1999 |
| GB | 2415256 A | 12/2005 |

OTHER PUBLICATIONS

PCT International Search Report and The Written Opinion of the International Searching Authority, or the Declaration, issued in International Application No. PCT/US2012/036377, mailed Oct. 22, 2012, 15 pages.

(Continued)

*Primary Examiner* — Mark Hellner
(74) *Attorney, Agent, or Firm* — John L. Wood (57) ABSTRACT

A device for conducting ultrasonic inspections comprises a base. In addition, the device comprises a probe housing pivotally coupled to the base with a suspension system. Further, the device comprises an ultrasonic probe disposed within the probe housing and configured to transmit ultrasonic signals. The suspension system is configured to permit the probe housing to pivot relative to the base to transmit ultrasonic signals in a plurality of directions.

23 Claims, 8 Drawing Sheets

(56) References Cited

OTHER PUBLICATIONS

Mexican Office Action dated Aug. 20, 2014; Mexican Application No. MX/a/2013/013035 (3 p.).

English Translation of Mexican Office Action dated Aug. 20, 2014; Mexican Application No. MX/a/2013/013035 (2 p.).

* cited by examiner

PIVOTING ULTRASONIC PROBE MOUNT AND METHODS FOR USE

CROSS-REFERENCE TO RELATED APPLICATIONS

This application claims benefit of U.S. provisional patent application Ser. No. 61/484,504 filed May 10, 2011, and entitled "Pivoting Ultrasonic Probe Mount and Methods for Use," which is hereby incorporated herein by reference in its entirety.

STATEMENT REGARDING FEDERALLY SPONSORED RESEARCH OR DEVELOPMENT

Not Applicable.

BACKGROUND

1. Field of Technology

This disclosure relates generally to ultrasonic inspection techniques and, more particularly, to apparatus and methods to perform subsea ultrasonic inspections.

2. Background Information

Ultrasound is a form of cyclical sound energy that travels as a waveform through a conducting medium (e.g., metal, liquid, body tissue, etc.). The frequency of an ultrasonic wave is above 20,000 Hz (or 20 KHz), generally greater than the upper threshold of human hearing.

The basic principles enabling ultrasonic technologies to be employed in inspection and diagnostic procedures are well-understood. Activating an ultrasonic probe (i.e. a device including a transmitter and a receiver of ultrasonic energy) positioned adjacent to the outer surface of an object of interest allows an image to be formed showing components internal to the object of interest. The ultrasonic wave is generated when an electric field is applied to one or more piezoelectric crystals located in the probe. Electrical stimulation causes mechanical distortion of the crystals causing them to vibrate and thereby produce sound waves (i.e. mechanical energy). An ultrasound image is generated when the pulsed sound waves emitted from the probe are transmitted into the object of interest, reflected off the interfaces of differing materials, and returned to the probe. The piezoelectric crystals of the probe, upon receiving the returning wave (i.e. echo), vibrate in response, and a transducer in the probe converts the mechanical energy from the vibrating crystals into an electrical signal, which is then processed and displayed as an image on a display screen.

A very common application of ultrasonic technologies is in the medical field where ultrasound enables a physician to visually observe the condition of a fetus, as well as tissue and other features internal to a patient's body. Due to its ability to image and display internal components of an object of interest, ultrasonic technologies have likewise been employed in the analysis and non-destructive testing of engineered structures, machines and other man-made products.

Subsea pipelines, products and structures associated with offshore oil and gas operations periodically require inspection and analysis. These objects may be located at the sea floor which, in some instances, may be 5,000-7,000 feet or more below the surface. At such depths, the water pressure exceeds 2,000 psi. Such depths and pressures may present difficult conditions in which to attempt ultrasonic inspection, and consequently, render some conventional equipment ineffective. For example, divers are unable to work at such depths, making the use of handheld ultrasonic probes impossible. Thus, carrying out ultrasonic inspection at such depths requires system components be carried to the sea floor and positioned by deep diving, remotely operated vehicles (ROV's) controlled by an operator at the surface. Not only may conventional ultrasonic technologies, systems and components be unable to withstand the subsea pressures encountered, but the components may be too fragile to be handled by the manipulating arms of the ROV. Further, accurately controlling the ROV from substantial distances, and using the ROV and its mechanical arms to position and operate components of conventional ultrasonic apparatus and systems, is impractical in many instances.

Accordingly, there remains a need in the art for improved devices and methods for employing ultrasonic inspection technologies subsea. Such devices and methods would be particularly well received if they offer the potential for use by subsea ROVs to ultrasonically inspect deepwater components.

BRIEF SUMMARY OF THE DISCLOSURE

These and other needs in the art are addressed in one embodiment by a device for conducting ultrasonic inspections. In an embodiment, the device comprises a base. In addition, the device comprises a probe housing pivotally coupled to the base with a suspension system. Further, the device comprises an ultrasonic probe disposed within the probe housing and configured to transmit ultrasonic signals. The suspension system is configured to permit the probe housing to pivot relative to the base to transmit ultrasonic signals in a plurality of directions.

These and other needs in the art are addressed in another embodiment by apparatus for performing ultrasonic inspections. In an embodiment, the apparatus comprises a base member having an aperture therethrough. In addition, the apparatus comprises a probe housing extending through the aperture. Further, the apparatus comprises an ultrasonic probe configured to transmit ultrasonic signals coupled to a first end of the probe housing. Still further, the apparatus comprises a plurality of springs coupling the probe housing to the base member.

These and other needs in the art are addressed in another embodiment by a method for conducting an ultrasonic inspection. In an embodiment, the method comprises (a) deploying an ultrasonic inspection device subsea. The device includes a base member, a probe housing pivotally coupled to the base member, and an ultrasonic probe coupled to the probe housing. In addition, the method comprises (b) attaching the device to a first location on a subsea object of interest. Further, the method comprises (c) emitting a first ultrasonic waveform from the ultrasonic probe into the object in a first direction. Still further, the method comprises (d) emitting a second ultrasonic waveform from the ultrasonic probe into the object in a second direction that is different than the first direction. Emitting the first ultrasonic waveform and emitting the second ultrasonic waveform are performed without moving the base member relative to the object.

Embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the disclosed embodiments of the invention, reference will now be made to the accompanying drawings in which.

DETAILED DESCRIPTION OF DISCLOSED EMBODIMENTS

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 1:
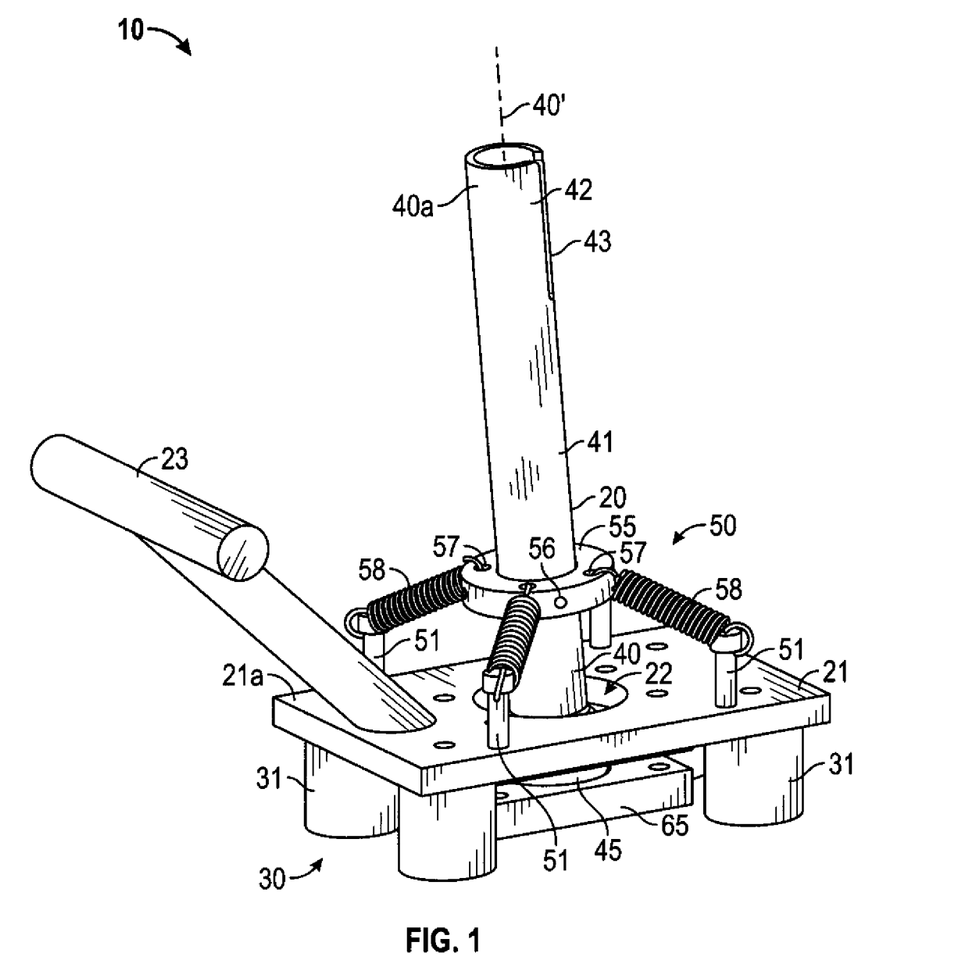
FIG. 1 is a perspective view of an embodiment of an ultrasonic inspection device in accordance with principles described herein.
Figure 2:
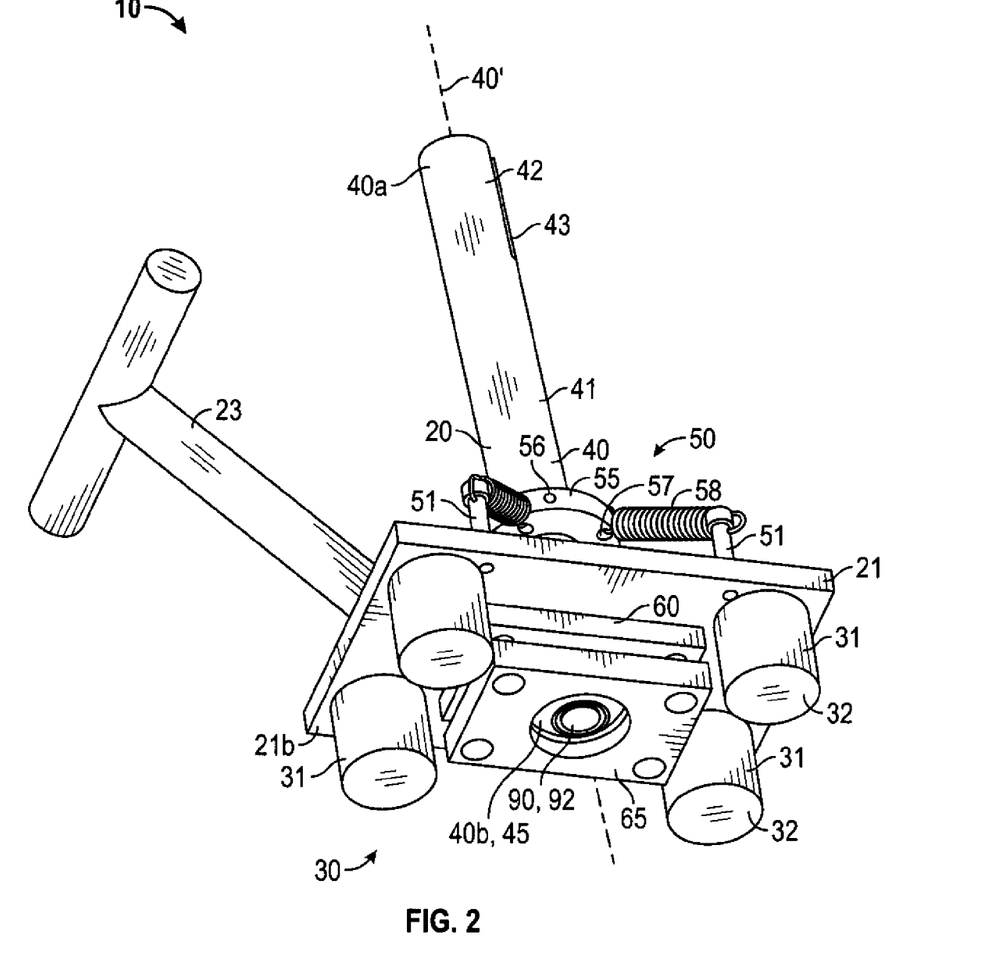
FIG. 2 is another perspective view of the ultrasonic inspection device of FIG. 1.
Figure 3:
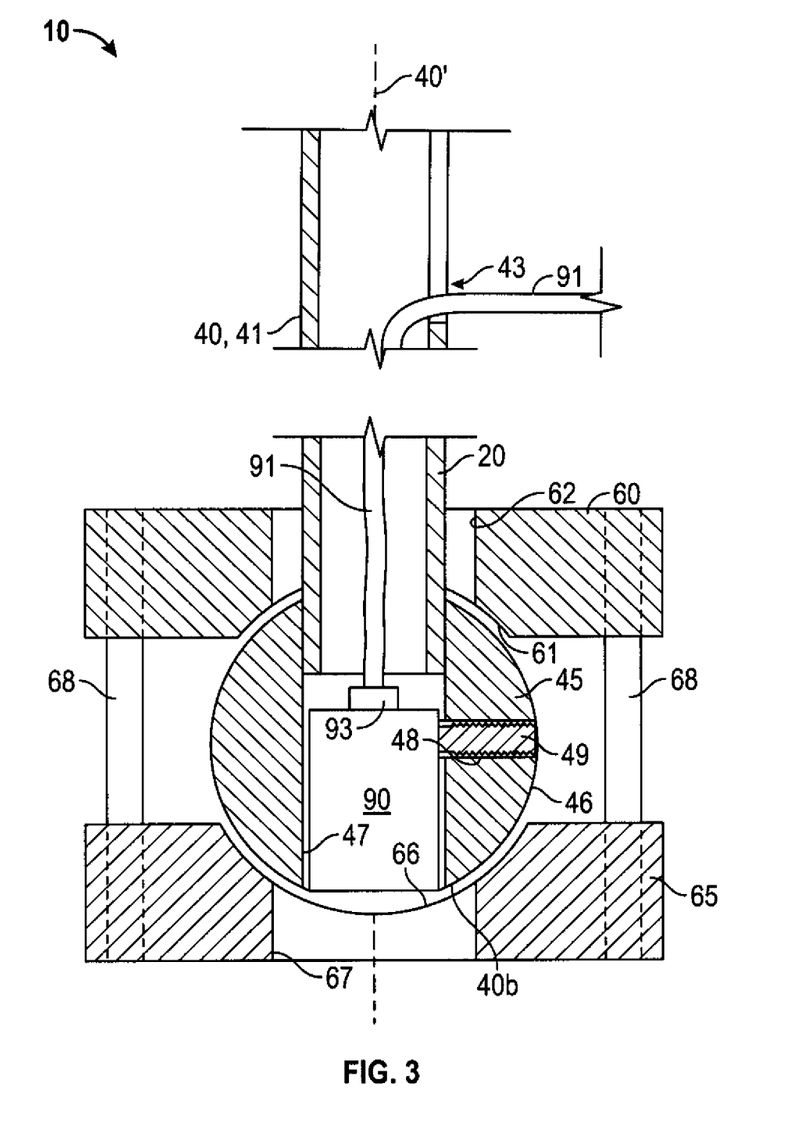
FIG. 3 is a partial cross-sectional view of the ultrasonic inspection device of FIG. 1 illustrating the probe housing and ball joint.

Referring now to FIGS. 1-3, an ultrasonic inspection device 10 is shown. As will be described in more detail below, device 10 is particularly suited for use subsea where it can be positioned and manipulated by one or more subsea ROVs. In this embodiment, device 10 includes a probe holding device or mount 20 and an ultrasonic probe 90 disposed therein. Mount 20 is used to position and manipulate probe 90 for ultrasonic inspection of an object of interest.

Mount 20 includes a rectangular base plate 21, a hold down system 30 coupled to plate 21, and a probe housing 40 pivotally coupled to base plate 21 with a suspension system 50.

Base plate 21 is a generally rigid plate having a first or upper surface 21a, a second or lower surface 21b, a through hole or aperture 22 extending between surfaces 21a, b, and a plurality of fastener-receiving holes for coupling hold down system 30 and suspension system 50 thereto. Probe housing 40 extends through aperture 22, and thus, aperture 22 may also be described as a "probe-receiving" hole or aperture. In this embodiment, aperture 22 is centrally positioned on base plate 21, however, in general, the probe-receiving aperture (e.g., aperture 22) may be positioned in other suitable locations on the base plate (e.g., plate 21). A handle 23 is mounted to base plate 21 and extends generally upward from upper surface 21a. Handle 23 is laterally spaced from probe housing 40 so as not to interfere with housing 40. In this embodiment, handle 23 is a T-handle that provides a convenient structure for an ROV to grasp to position and manipulate device 10. Base plate 21 and handle 23 are preferably made of a rigid material(s) suitable for subsea use such as aluminum, stainless steel, carbon steel, or inconel.

Figure 5:
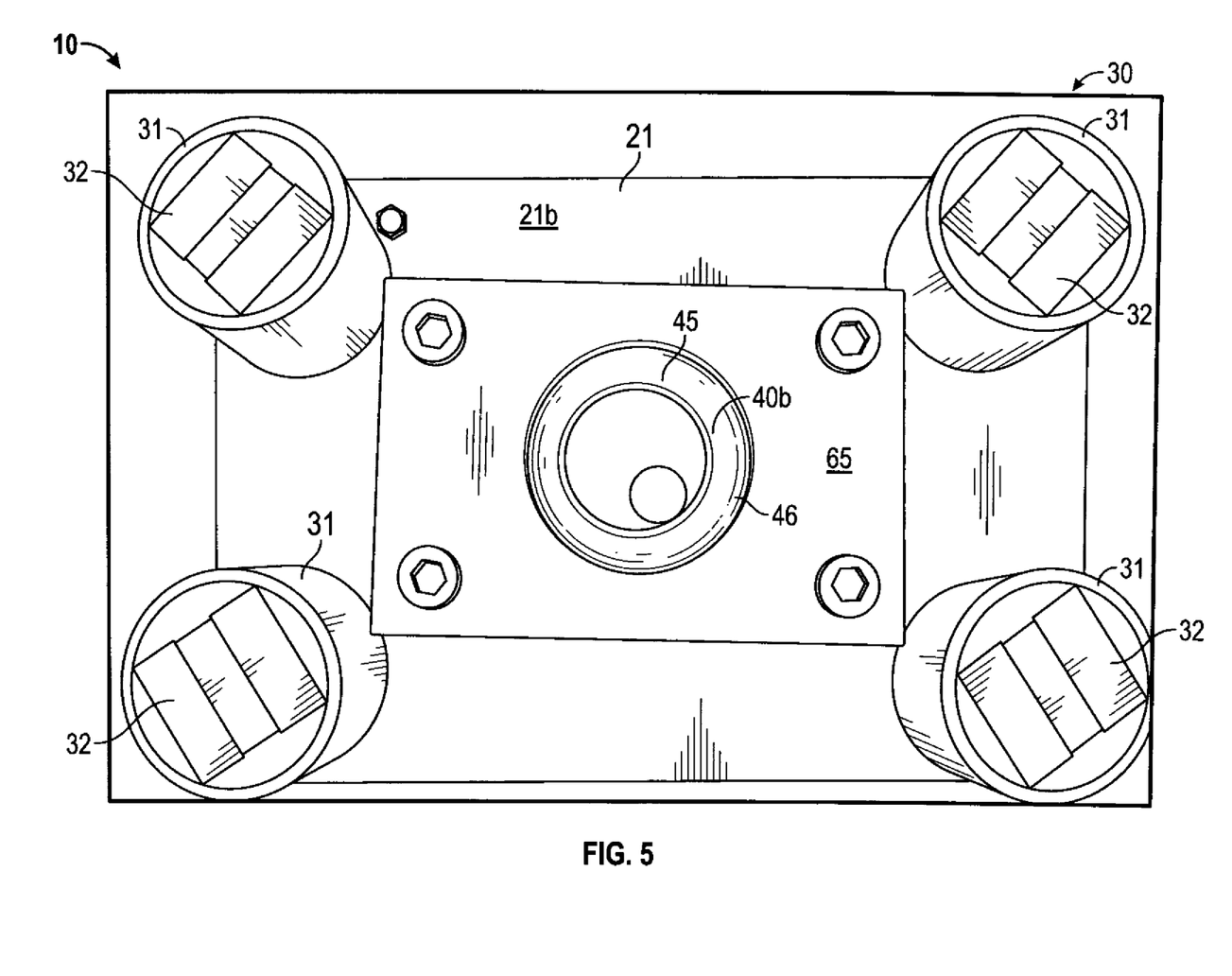
FIG. 5 is a bottom view of the ultrasonic inspection device of FIG. 1.

Referring now to FIGS. 1, 2, and 5, hold down system 30 is mounted to the bottom of base plate 21. In general, hold down system 30 functions to attach device 10 to the object of interest and maintain device 10 in the desired location once attached. Hold down system 30 includes a plurality of parallel legs 31 extending from lower surface 21b of base plate 21 and a plurality of magnets 32 coupled to the lower ends of legs 31 distal plate 21. As best shown in FIG. 5, in this embodiment, legs 31 are cylindrical tubes and magnets 32 are positioned within the lower open ends of each tubular leg 31.

Magnets 32 are used in this exemplary embodiment to couple device 10 to an object made of ferro-magnetic metal. It should be appreciated that inclusion of magnets 32 to attach device 10 to the object of interest relieves an ROV from otherwise having to hold the device 10 in position during the subsea ultrasonic inspection. Although other types of magnets can be employed, magnets 32 are preferably rare earth Neodinium-Iron magnets.

Referring now to FIGS. 1-4, probe housing 40 has a central or longitudinal axis 40', a first or upper end 40a, and a second or lower end 40b opposite end 40a. In this embodiment, housing 40 includes a ball joint 45 at lower end 40b and an elongate extension member 41 extending from ball joint 45 to upper end 40a. As will be described in more detail below, housing 40 can be pivoted about the center of ball joint 45 relative to base plate 21 to vary the orientation of probe 90 and the direction of imaging. Extension member 41 and ball joint 45 are each preferably made of rigid material(s) suitable for subsea use such as aluminum, stainless steel, carbon steel, or inconel.

Extension member 41 extends axially from end 40a and ball joint 45 is coupled to extension member 41 at end 40b. Extension member 41 is an elongate tubular extending through aperture 22 (i.e., member 41 has an outer diameter less than the diameter of aperture 22). As best shown in FIG. 3, a through hole or aperture 43 extends radially through extension member and receives a probe cable 91 coupled to probe 90 disposed within ball joint 45.

At upper end 40a, extension member 41 comprises a handle 42, which, in this embodiment, is an extension of extension member 41. Handle 42 provides a grasping point from which a subsea ROV can manipulate extension member 41 and probe housing 40, and thereby direct probe 90 in the desired orientation.

Ball joint 45 has a spherical outer surface 46, a central through bore 47 for receiving probe 90, and a bore 48 for threadingly receiving a set screw 49. Bore 47 extends axially through ball joint 45, and bore 48 extends radially through ball joint 45 from surface 46 to bore 47. Extension member 41 is threaded into bore 47 such that extension member 41 does not move rotationally or translationally relative to joint 45 during subsea inspection operations. Set screw 49 is threaded into a bore 48 and has a radially inner end that engages probe 90 disposed within bore 47, thereby securing probe 90 within ball joint 45. Although probe 90 is positioned and retained in central bore 47 with set screw 49 in this embodiment, in other embodiments, probe 90 may be secured within bore 47 by other suitable means (e.g., adhesive).

Referring now to FIG. 3, as previously described, ultrasonic probe 90 is disposed in bore 47 of ball joint 45 at lower end 40b of housing 40, and is held in place with set screw 49. In general, ultrasonic probe 90 may be any commercially available ultrasonic probe capable of emitting and receiving ultrasonic signals. For subsea use, probe 90 and cable 91 are preferably water tight and rated for subsea use up to the depth at which the ultrasonic investigation is to be performed. One example of a suitable ultrasonic probe for use subsea is a deepwater immersion ultrasonic probe, operating at 3 MHz, as supplied by Phoenix Ultrasonic Systems Ltd. of Cheshire, UK.

Probe 90 houses one or more piezoelectric crystals positioned axially adjacent an exposed sensing end 92 at end 40b of housing 40 so as to be able to receive and transmit ultrasonic energy. In particular, probe 90 is positioned and oriented to emit ultrasonic signals from end 92 in the general direction of a projection of axis 40'. Probe cable 91 is connected to probe 90 with a watertight connector 93, and extends from probe 90 up the inside of ball joint 45 and extension member 41 to aperture 43, where cable 91 exits housing 40.

Referring again to FIGS. 1 and 2, suspension system 50 supports probe housing 40 within aperture 22 of base plate 21 while allowing housing 40, and hence ball joint 45, to pivot relative to base plate 21 to the desired degree. In this embodiment suspension system 50 includes a plurality of standoffs 51 extending upward from surface 21a of base plate 21, a ring 55 mounted to extension member 41, a plurality of springs 58 extending between standoffs 51 and ring 55, a first or upper probe mounting plate 60 and a second or lower probe mounting plate 65. Standoffs 51 are elongate cylindrical members uniformly circumferentially spaced about aperture 22 and attached to base plate 21. In this embodiment, each standoff 51 has an axially aligned internally threaded bore that receives a threaded fastener disposed through a hole in base plate 21.

Figure 4:
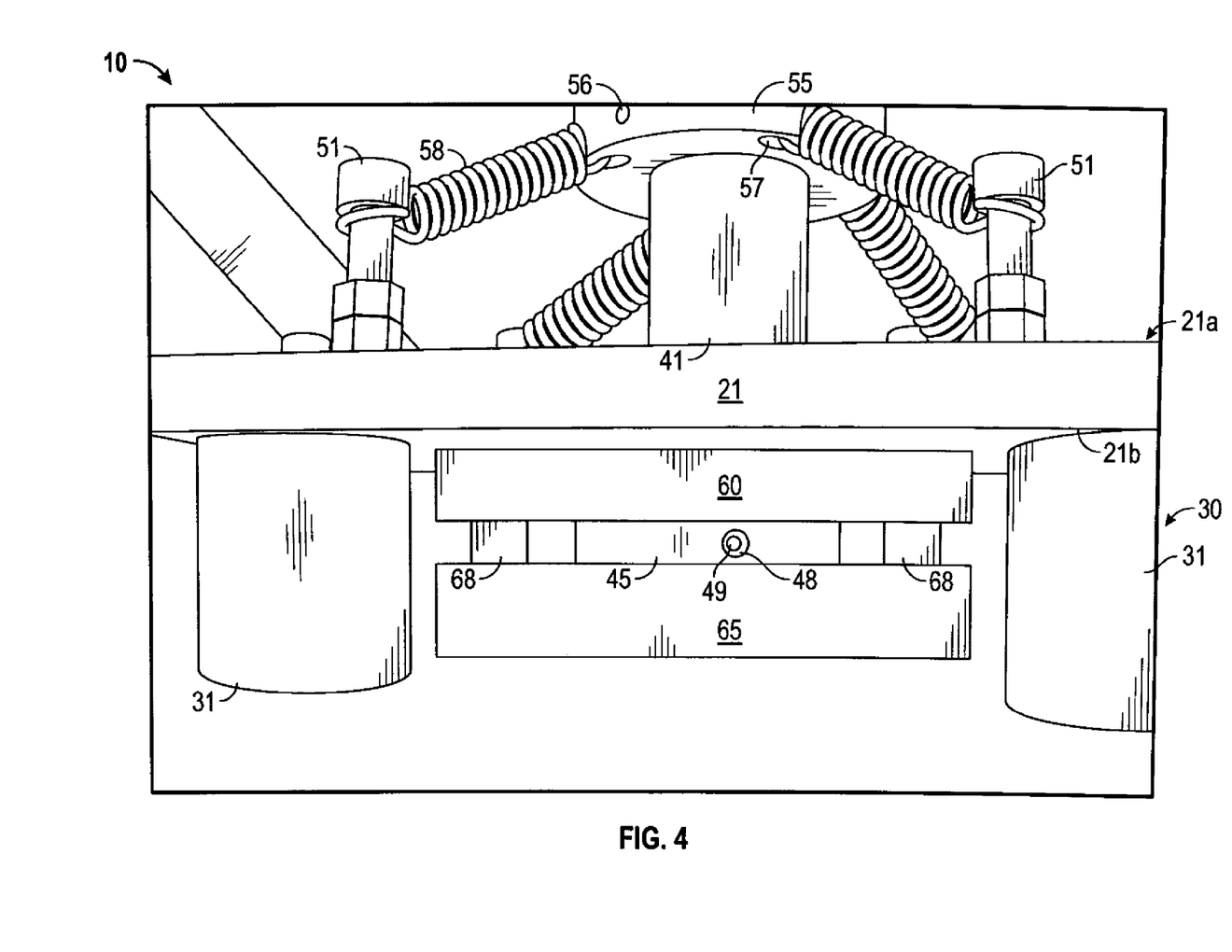
FIG. 4 is a partial side view of the ultrasonic inspection device of FIG. 1.

As best shown in FIGS. 2 and 4, ring 55 is disposed about and slidingly engages extension member 41. Thus, ring 55 has a cylindrical inner surface disposed at a diameter that is substantially the same or slightly greater than the outer diameter of extension member 41. The axial position of ring 55 on extension member 41 is locked by a plurality of circumferentially spaced set screws threaded through radially oriented bores 56 in ring 55 and into engagement with extension member 41. In this embodiment, four uniformly circumferentially spaced bores 56 and corresponding set screws are provided.

Ring 55 also includes four uniformly circumferentially spaced axially oriented bores 57 extending therethrough. One end of each spring 58 is attached to ring 55 via bores 57. The opposite end of each spring 58 is attached to one standoff 51 via a hole in the upper end of the corresponding standoff 51. Thus, springs 58 extend between bores 57 in ring 55 and the upper ends of standoffs 51. Each bore 57 is radially aligned with one standoff 51, and one spring 58 extends radially between each set of radially aligned bores 57 and standoffs 51. Ring 55 is positioned axially above standoffs 51, and thus, each spring 58 extends radially outward and axially downward moving from ring 55 towards the corresponding standoff 51. Consequently, springs 58 bias probe housing 40 axially downward and towards a centered position shown in FIGS. 1-3 with axis 40' oriented perpendicular to base plate 21 and coaxially aligned with the central axis of aperture 22. This centered position is also referred to herein as the probe's "0-degree" position or "centrum." During use, a radial force (i.e., a force perpendicular to axis 40') is applied to extension member 41 via handle 42 to generate a moment that pivots probe housing 40 (about the center of ball joint 45) from the centrum position to vary the direction of the ultrasonic signals transmitted by probe 90. However, suspension system 50 functions to bias probe housing 40 back to the centrum position upon release of such force. Thus, probe housing 40 operates in a similar manner as a joystick that is biased to the centrum position.

Referring now to FIGS. 2 and 3, ball joint 45 slidingly engages plates 60, 65, which retain ball joint 45 in mount 20. In this embodiment, mounting plates 60 and 65 are formed of Deiron® plastic, however, other materials may be used. Upper probe mounting plate 60 is coupled to base plate 21 and is positioned between lower probe mounting plate 65 and base plate 21. Plate 60 includes a concave, generally spherically recess 61 in its lower surface and a through bore or aperture 62 extending axially upward from recess 61 through plate 60. Plate 60 is positioned such that aperture 62 is coaxially aligned with aperture 22. Aperture 62 in plate 60 has a smaller diameter than aperture 22 in base plate 21, and is sized to limit the pivot angle to which probe housing 40 can pivot in any given direction from the 0-degree position before extension member 41 contacts plate 60.

Lower probe mounting plate 65 includes a concave, generally spherically recess 66 in its upper surface and a through bore or aperture 67 extending axially downward from recess 66 through plate 65. Plate 65 is coupled to base plate 21 by standoffs 68, which extend through upper plate 60. In addition, plate 65 is positioned such that recess 66 and aperture 67 are coaxially aligned with apertures 22, 62. Ball joint 45 is disposed within curved recess 66 and is biased into sliding contact therewith via springs 58.

Figure 6:
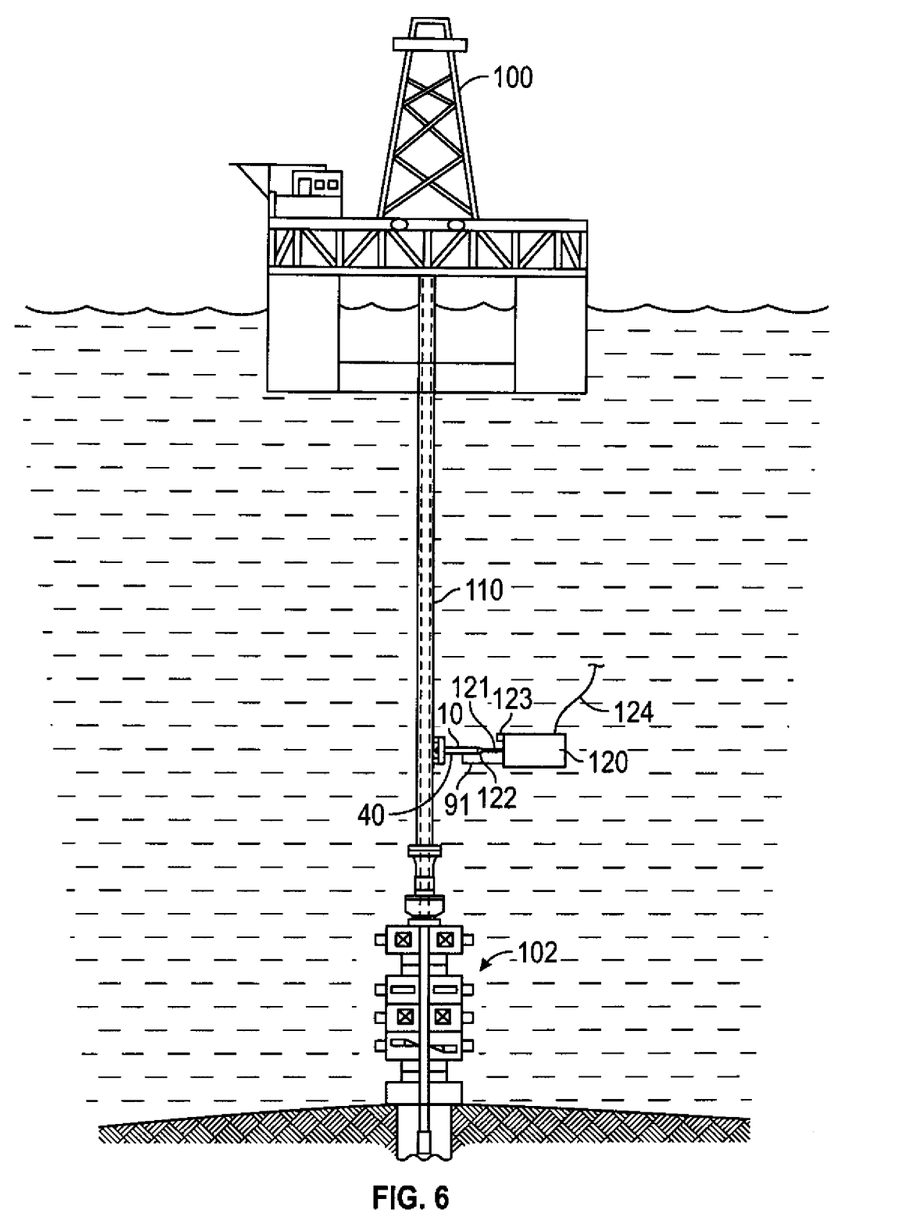
FIG. 6 is a schematic view illustrating the subsea deployment and use of the ultrasonic inspection device of FIG. 1.
Figure 7:
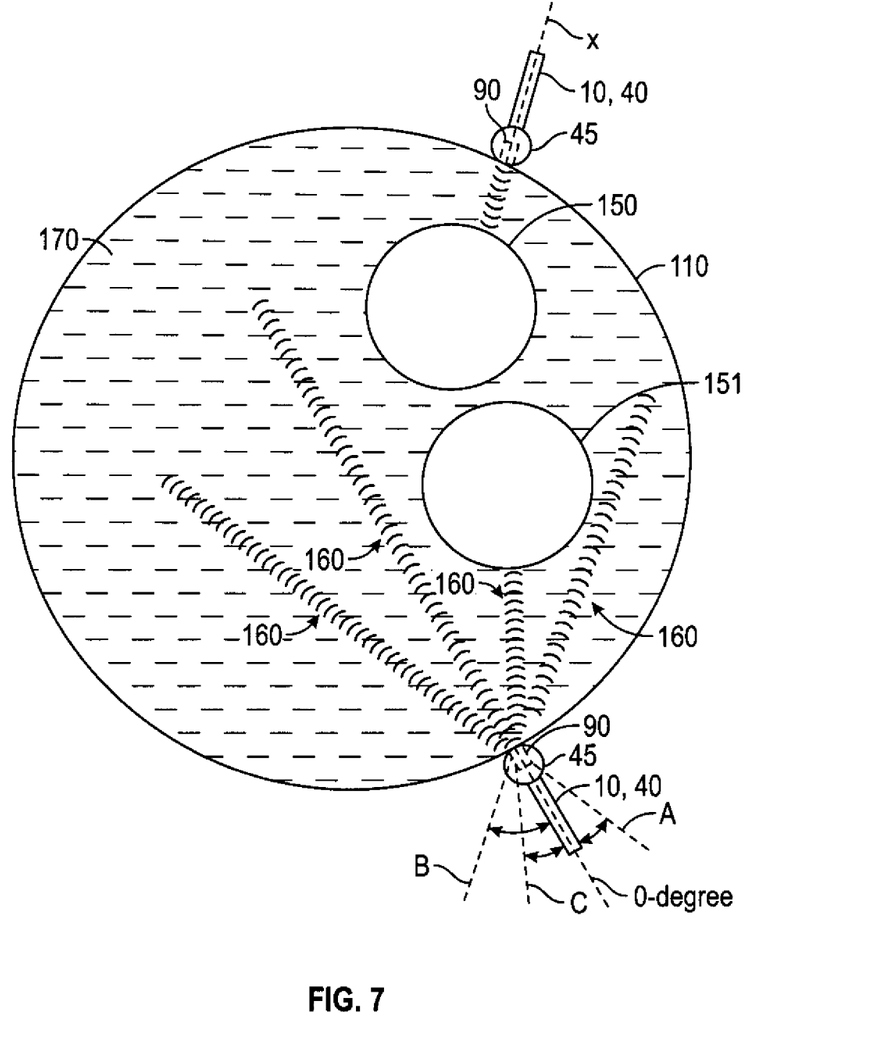
FIG. 7 is a schematic cross-sectional view of the ultrasonic inspection device of FIG. 6 taken along section 7-7.
Figure 8:
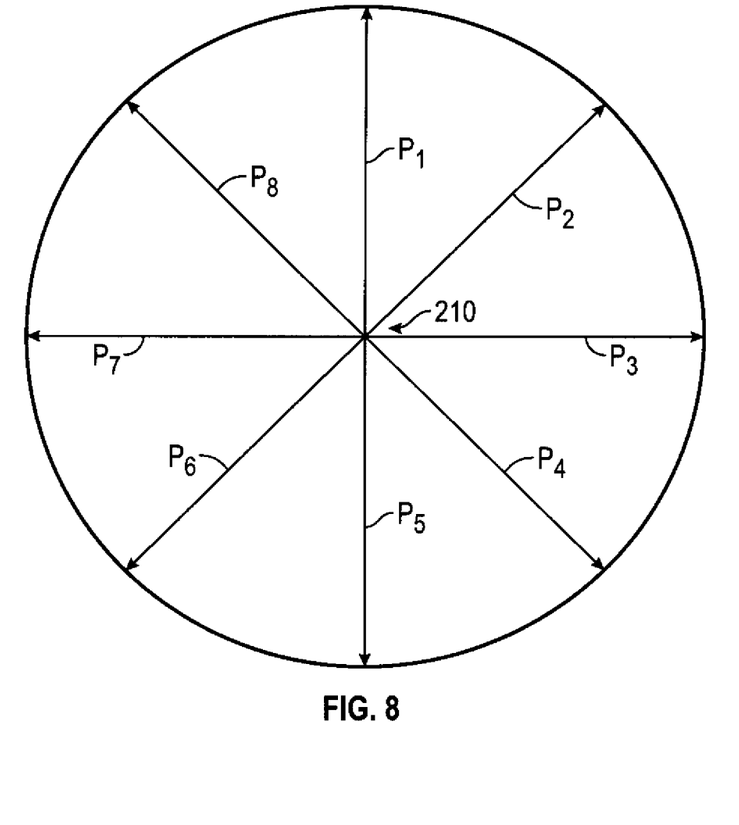
FIG. 8 is a schematic view illustrating the 360 degree range of motion provided to the ultrasonic probe in the ultrasonic inspection device of FIG. 1.

Referring now to FIGS. 6-8, an embodiment of a method for using device 10 to perform a subsea ultrasonic inspection is illustrated. In general, device 10 is deployed subsea from a surface vessel 100 to a position adjacent an object of interest 110 to be ultrasonically inspected. In this exemplary embodiment, vessel 100 is a drilling platform and object of interest 110 is a riser extending from a blow out preventer (BOP) stack 102 at the sea floor to vessel 100. As is known in the art, a riser (e.g., riser 110) is a tubular member through which one or more other tubular members such as drillstrings and production tubing are typically deployed, and thus, device 10 can be used to ultrasonically inspect such tubulars within riser 110. However, in general, device 10 may be deployed from any type of offshore vessel including, without limitation, a drilling platform, a boat, or a barge, and further, the object of interest may be any of a myriad of components. The devices and methods described herein have particular utility in examining components internal to another device or structure, and to determine the position and/or condition of the internal components. Thus, merely as further examples, the methods and devices described herein may be advantageously employed to determine the location of a pipeline pig that has become inoperative somewhere inside a underwater pipeline, or to determine the position of pistons housed within hydraulic cylinders. Moreover, embodiments described herein may be deployed to investigate malfunctioning equipment or to perform periodic maintenance on subsea equipment.

Referring now to FIG. 6, according to this exemplary method, device 10 is transported subsea to riser 110. For subsea deployment and operation, one or more remote operated vehicles (ROVs) are preferably employed to position, manipulate, operate, and monitor device 10. In this embodiment, one ROV 120 is shown. ROV 120 includes an arm 121 having a claw 122, a subsea camera 123 for viewing the subsea operations (e.g., the relative positions of device 10 and the object of interest, the orientation of housing 40, the movement of claw 122 and arm 121, etc.), and an umbilical 124. Streaming video and/or images from camera 123 is communicated to the surface or other remote location via umbilical 124 for viewing on a live or periodic basis. Arm 121 and claw 122 are controlled via commands sent from the surface or other remote location to ROV 120 through umbilical 124.

Using manipulator arm 121, ROV 120 grasps handle 23 and then positions device 10 on riser 110 at a location where an inspection of riser 110 and its internals is desired. Magnets 32 hold device 10 in position against the ferro-magnetic riser 110. Power is supplied to probe 90 via power conductors contained within probe cable 91, which is coupled to ROV 120. Similarly, control and data signals are communicated between probe 90 and ROV 120 via separate conductors contained in probe cable 91. In turn, power as well as data and control signals are communicated between ROV 120 and surface vessel 100 via ROV umbilical 124. When the imaging is to begin, and with device 10 secured to riser 110 by magnets 32, ROV arm 121 releases handle 23 and then grasps manipulating handle 42 so as to be able to pivot probe housing 40 and probe 90 in order to emit ultrasound waveforms and collect ultrasound echoes in various directions.

Referring now to the schematic representation shown in FIG. 7, with probe housing 40 and probe 90 in the initial 0-degree position, probe 90 is activated in order to emit ultrasonic waveforms and to receive reflected waveforms that reflect back to probe 90. Assuming, in this example, that the inspection is being conducted to determine the location and/or condition of exemplary tubing strings 150 and 151 disposed within riser 110, when probe 90 is in its centered 0-degree position, ultrasonic waves 160 emitted from probe 90 may completely miss tubing strings 150, 151. This may be the case because probe 90 is too far out of alignment with tubing strings 150, 151, or because ultrasonic waves 160 are refracted at the interface between fluid 170 in riser 110 and the metal of riser 110 to such an extent that sound waves 160 do not impact tubing strings 150, 151. Further, sound waves 160 may impact tubing strings 150, 151, but do so at such an extreme angle that the echoes do not return to probe 90, but instead are reflected in directions that "miss" probe 90. In real time, the echoes or "returns" detected by probe 90 are monitored by operators in vessel 100.

After determining that probe 90, in its initial orientation, has not detected the presence of tubing strings 150, 151, operators direct ROV 120 to pivot probe housing 40 to position probe 90 to scan in other directions within riser 110. For example, ROV manipulating arm 121 may be directed to pivot probe housing 40 to a position "A" as shown in FIG. 7. At position "A", ultrasound waves 160 are again emitted and return echoes listened for. In this example, tubing strings 150, 151 are still not be detected as position "A" is significantly out of alignment with strings 150, 151, and thus, ROV arms 121 release manipulating handle 42, thereby allowing probe housing 40 and probe 90 to return to the 0-degree position. Next, in this example, the ROV arm 121 is manipulated to pivot housing 40 to assume a different position "B" shown in FIG. 7. In position "B," emitted sound waves once again "miss" tubing strings 150, 151 or will send reflected waves in a direction that will miss probe 90. However, device 10 allows ultrasonic waves 160 to be generated at multiple positions, not merely at the extreme reaches of the arc in which probe housing 40 is permitted to swing before impinging plate 60. Thus, in this example, operators next maneuver ROV arm 121 to pivot probe housing 40 to yet another different position "C" shown in FIG. 7, a position in which sound waves 160 impact tubing string 151 at an angle sufficient to generate reflected waves back to probe 90, thereby allowing the detection and location identification of string 151 within riser 110. If tubing string 150 cannot be located with device 10 positioned in the first location on riser 110, ROV 120 can be directed to reposition device 10 elsewhere along riser 110 (different axial and/or circumferential position along riser 110). For example, ROV 120 may reposition device 10 to a position "X" shown in FIG. 7. Using the same method described above, with device 10 stationary on riser 110, probe housing 40 is swung to multiple positions until the tubing string 150 is located. When the ultrasonic investigation is complete, ROV 120 grasps handle 23, disengages mount 20 from its position on riser 110, and returns the mount 20 to the surface vessel 100.

As previously described, FIG. 7 schematically illustrates the pivoting of probe housing 40 through a path disposed in a single plane. However, it is to be understood that device 10 permits probe housing 40 to be pivoted about the center of ball joint 45 anywhere within a right circular cone defined by aperture 62 and having an apex at the center of ball joint 45. At the 0-degree position, axis 40' of probe housing 40 is coincident with the central axis of such a cone. The conical surface defining the cone is preferably positioned at an angle of at least 25°, and more preferably 30°, from the central axis of the cone and the 0-degree position. With axis 40' oriented at a maximum angle of 30° relative to the 0-degree position, the maximum incident angle of the ultrasonic beam with the surface of the object of interest (measured from a line perpendicular to the surface of the object of interest) will also be about 30°. With a steel object of interest, ultrasonic refraction may begin to occur at incident angles greater than about 30°.

Moving now to FIG. 8, with a point 210 representing the center of ball joint 45, probe housing 40 can be pivoted about point 210 along any of exemplary paths P1-P8, as well as along any path or to any position in or between paths P1-P8, so as to take ultrasonic examinations in various directions. For instance, in the 0-degree position with extension member 41 extending perpendicular to and out of the page in FIG. 8, probe housing 40 can be pivoted about point 210 by swinging member 41 in the direction of P1, P2, P3, etc. In the 0-degree position, probe 90 is positioned to emit ultrasonic waves, and hence perform examinations, in a direction perpendicular to and into the page in FIG. 8, however, with member 41 swung in any direction from the 0-degree position, probe 90 is positioned to emit ultrasonic waves, and hence perform examinations, in a direction generally opposite member 41 and into the page in FIG. 8. For example, with member 41 swung in the direction of P7 from the 0-degree position, probe 90 is positioned to emit ultrasonic waves generally in the direction of P2 and into the page of FIG. 8. Thus, in the 0-degree position, probe 90 emit ultrasonic waves perpendicular to and into the page of FIG. 8, but when member 41 is swung from the 0-degree position, probe 90 is re-oriented to emit ultrasonic waves into the page of FIG. 8 at an acute angle and generally away from member 41.

An ultrasonic waveform refracts when passing obliquely across boundaries of materials having differing acoustic properties. In other words, and using the embodiment of FIG. 7 as an example, the waveform that emerges at the inside surface of the riser wall will have refracted and will no longer be traveling in the precise direction as when it was emitted by probe 90. Accordingly, the pivoting feature of probe mount 20 allows the creation of a waveform that can be "steered" through a range of angles. Pivoting probe housing 20 back and forth and in a 360 degree path creates a sweeping directional beam that can reflect off of and therefore detect embedded objects that may be in places other than as expected, thereby increasing the chances of detecting reflections from the internal objects. Thus, device 10 and associated methods of operation enable substantial flexibility in conducting ultrasonic investigations.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A device for conducting ultrasonic inspections, the device comprising:
    a base including an aperture;
    a probe housing extending through the aperture of the base, wherein the probe housing is pivotally coupled to the base with a suspension system;
    an ultrasonic probe disposed within the probe housing and configured to transmit ultrasonic signals;
    wherein the suspension system is configured to permit the probe housing to pivot relative to the base to transmit ultrasonic signals in a plurality of directions, and wherein the suspension system is configured to bias the probe housing from a pivoted position with a central axis of the probe housing out of coaxial alignment with a central axis of the aperture to a centrum position with the central axis of the probe housing coaxially aligned with the central axis of the aperture.

2. The device of claim 1, wherein the probe housing includes a ball joint, wherein the ultrasonic probe is mounted in a through bore of the ball joint.

3. The device of claim 2, wherein the ball joint is positioned between a first probe mount plate and a second probe mount plate, wherein each probe mount plate is coupled to the base; and
    wherein the ball joint slidingly engages a mating concave recess in the first probe mount plate and a mating concave recess in the second probe mount plate.

4. The device of claim 3,
    wherein the suspension system includes:
        a plurality of standoffs coupled to the base and circumferentially spaced about the aperture;
        a ring disposed about the probe housing; and
        a spring extending from each standoff to the ring.

5. The device of claim 4, wherein the springs bias the ball joint into engagement with the second probe mount plate.

6. The device of claim 1, further comprising a hold down system configured to couple the base to an object of interest.

7. The device of claim 6, wherein the hold down system includes a plurality of legs extending from the base and a plurality of magnets, wherein one of the magnets is coupled to an end of each leg.

8. The device of claim 1, wherein the central axis of the probe housing is oriented perpendicular to the base with the probe housing in the centrum position.

9. The device of claim 1, wherein the suspension system is configured to permit the probe housing to pivot from a neutral position to a second position oriented at an angle of at least 25° from the neutral position in at least both a first direction and a second direction, wherein the first and second directions are 180° opposite one another relative to the axis.

10. The device of claim 9, wherein the suspension apparatus is configured to permit the probe housing to pivot from a neutral position to a second position oriented at an angle of at least 30°.

11. An apparatus for performing ultrasonic inspections, comprising:
    a base member having an aperture therethrough;
    a probe housing extending through the aperture;
    an ultrasonic probe configured to transmit ultrasonic signals coupled to a first end of the probe housing; and
    a plurality of circumferentially-spaced springs disposed about the probe housing, wherein each spring has a first end coupled to the probe housing and a second end coupled to the base member.

12. The apparatus of claim 11, further comprising a plurality of legs coupled to the base member and a plurality of magnets coupled to the legs.

13. The apparatus of claim 11, further comprising a handle coupled to the base member, wherein the handle is configured to be manipulated by a subsea ROV.

14. The apparatus of claim 11, wherein the probe housing includes a ball joint, wherein the probe is disposed within the ball joint and the ball joint is rotatably coupled to the base member.

15. The apparatus of claim 14, further comprising a manipulating handle coupled to the probe housing and configured to pivot the probe housing and rotate the ball joint.

16. The apparatus of claim 11, wherein the plurality of springs are configured to bias the probe housing to a central position coaxially aligned with the aperture.

17. The apparatus of claim 14, wherein the plurality of springs are positioned on a first side of the base member and the ball joint is positioned on a second side of the base member opposite the first side of the base member.

18. A method for conducting an ultrasonic inspection, comprising:
    (a) deploying an ultrasonic inspection device subsea, the device including a base member, a probe housing pivotally coupled to the base member, and an ultrasonic probe coupled to the probe housing;
    (b) attaching the device to a first location on a subsea object of interest;
    (c) emitting a first ultrasonic waveform from the ultrasonic probe into the object in a first direction;
    (d) emitting a second ultrasonic waveform from the ultrasonic probe into the object in a second direction that is different than the first direction;
    wherein (c) and (d) are performed without moving the base member relative to the object.

19. The method of claim 18, wherein (d) comprises pivoting the probe housing relative to the base member with a subsea ROV.

20. The method of claim 18, wherein (b) comprises magnetically attaching the device to the object.

21. The method of claim 18, further comprising:
  (e) emitting a third ultrasonic waveform from the ultrasonic probe into the object in a third direction that is different from the first direction and the second direction, wherein (c), (d), and (e) are performed without moving the base member relative to the object.

22. The method of claim 18, wherein (a) comprises deploying the ultrasonic inspection device subsea to investigate a malfunctioning piece of subsea equipment or perform maintenance on a piece of subsea equipment.

23. The method of claim 18, wherein the probe housing is pivotally coupled to the base member with a suspension system configured to permit the probe housing to pivot relative to the base member;
  wherein the suspension system is configured to bias the probe housing from a pivoted position with a central axis of the probe housing out of coaxial alignment with a central axis of the aperture to a centrum position with the central axis of the probe housing coaxially aligned with the central axis of the aperture.

* * * * *